US00PP29572P3

(12) United States Plant Patent
Kordes

(10) Patent No.: US PP29,572 P3
(45) Date of Patent: Aug. 7, 2018

(54) MINIATURE ROSE PLANT NAMED 'KORPOT073'

(50) Latin Name: *Rosa hybrida*
Varietal Denomination: KORpot073

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/530,708

(22) Filed: Feb. 17, 2017

(65) Prior Publication Data

US 2017/0374774 P1 Dec. 28, 2017

Related U.S. Application Data

(60) Provisional application No. 62/493,177, filed on Jun. 23, 2016.

(51) Int. Cl.
*A01H 5/02* (2018.01)

(52) U.S. Cl.
USPC ..... Plt./129
CPC ..... *A01H 5/0222* (2013.01)

(58) Field of Classification Search
USPC ..... Plt./116, 129
See application file for complete search history.

*Primary Examiner* — Susan McCormick Ewoldt
(74) *Attorney, Agent, or Firm* — Samuel R. McCoy, Jr.

(57) ABSTRACT

'KORpot073' is a new and distinct variety of *Rosa hybrida* which is characterized by the combination of a compact growth habit, moderately vigorous growth, and an abundance of red, very double flowers. The new variety propagates successfully by stem cuttings and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORpot073'.

STATEMENT REGARDING PRIOR DISCLOSURES BY THE INVENTOR UNDER 37 C.F.R. 1.77(B)(6)

The first public disclosure of the claimed plant, in the form of an offer for sale, was made by the wholesale nursery Rosa Danica, in Denmark, in August of 2015. In November of 2015, Rosa Danica published information pertaining to the claimed plant on their website and subsequently displayed the claimed plant at a tradeshow in Essen, Germany in January of 2016. Rosa Danica obtained the claimed plant, and all information relating thereto, from the inventor. 'KORpot073' was not publically available or sold prior to the one year anniversary of the filing date of the provisional application to which benefit is claimed.

BACKGROUND OF THE INVENTION

The present invention relates to a new and distinct *Rosa hybrida*, miniature rose cultivar, which has been given the variety denomination of 'KORpot073'.

Parentage: 'KORpot073' is a seedling selection which resulted from the controlled pollination of an unnamed *Rosa hybrida* seedling developed and owned by the same inventor, the seed parent, and *Rosa hybrida* 'RUId155a' (not patented in the United States), the pollen parent, during the summer of 2012. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2013 from the seedling beds due to its superior characteristics and asexually propagated for further evaluation. This new and distinctive rose variety was given the name 'KORpot073'.

Asexual Reproduction: The first asexual propagation of 'KORpot073', by way of stem cuttings, was performed in June of 2013 at the inventor's nursery in Offenseth-Sparrieshoop, Germany. Subsequently, 'KORpot073' has been successfully propagated by stem cuttings in Jackson County, Oreg. These initial and other subsequent propagations conducted in controlled environments demonstrate that 'KORpot073' reproduces true to type in successive generations of asexual reproduction.

SUMMARY OF THE INVENTION

The following characteristics have been repeatedly observed and represent the distinguishing characteristics of the new *Rosa hybrida* cultivar 'KORpot073'. These traits, in combination, distinguish 'KORpot073' as a new and distinct cultivar.

1. *Rosa hybrida* 'KORpot073' exhibits a compact growth habit; and
2. *Rosa hybrida* 'KORpot073' exhibits moderately vigorous growth; and 3. *Rosa hybrida* 'KORpot073' exhibits a very double petal count; and
4. *Rosa hybrida* 'KORpot073' exhibits a medium flower size for a miniature rose; and
5. *Rosa hybrida* 'KORpot073' exhibits a red flower color at anthesis.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot073', taken from ten month old plants.

DETAILED BOTANICAL DESCRIPTION

The following is a detailed botanical description of a new and distinct variety of *Rosa hybrida* known as 'KORpot073', based upon field observations made in October of 2016, from ten month old container-grown plants in a greenhouse environment in Jackson County, Oreg. Those skilled in the art will appreciate that certain characteristics will vary with older or, conversely, with younger plants. 'KORpot073' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2001 edition except where common terms of color are used.

A botanical description of 'KORpot073' and comparisons with other varieties of *Rosa hybrida* are provided below.

General plant description:

*Growth rate.*—Moderately vigorous.

*Growth habit.*—Compact.

*Mature dimensions.*—20 cm tall and 15 cm wide, on average, when grown as a 10 cm nursery pot.

*Cold hardiness.*—Unknown.

*Propagation.*—Stem cuttings.

*Disease resistance.*—Above average resistance to powdery mildew (*Sphaerotheca pannosa*) and *Botrytis* diseases under normal growing conditions in Jackson County, Oreg.

Root system:

*Type.*—Fibrous root system with many root hairs.

*Branching.*—Freely branched.

*Density.*—Moderately dense rooting.

*Distribution.*—Roots distributed uniformly throughout the soil profile, from shallow to deep.

Stems:

*Stem color, immature stems.*—Yellow-Green Group 146C.

*Stem color, mature stems.*—Yellow-Green Group 146B.

*Anthocyanin intonations.*—Greyed-Purple Group 183B intonations are present on juvenile stems.

*Stem surface texture.*—Both immature and mature stems exhibit a smooth texture.

*Stem dimensions.*—Typical mature stems are approximately 12 cm long and 0.3 to 0.4 cm in diameter.

*Prickles.*—Incidence — Present; 12 to 15 prickles per 10 cm of stem, on average. Size — Average length is 3 mm. Immature prickle color — Greyed-Purple Group 183B. Mature prickle color — Greyed-Brown Group 199B. Anthocyanin intonations — Occasionally with a limited amount of Greyed-Purple Group 185B intonations. Shape — Concave. Texture — Smooth.

Leaves:

*Arrangement.*—Imparipinnate compound leaves; mature axillary leaves consisting of 5 leaflets.

*Attachment.*—Petiolate.

*Dimensions.*—80 mm long and 5.0 mm wide, on average.

*Abundance.*—Not abundant; 30 to 40 leaves.

*Stipules.*—Size — 14 mm long and 5 mm wide. Stipule color — Yellow-Green Group 146C. Anthocyanin intonations — None. Stipitate glands — Very limited number. Margins — Serrulate. Texture, adaxial surfaces — Glabrous. Texture, abaxial surfaces — Glabrous. Apex — Apiculate. Base — Winged; fused to the petiole.

*Petiole.*—Length — 6.0 mm. Diameter — 1.0 to 1.5 mm. Petiole color, adaxial surface — Yellow-Green Group 146A. Petiole color, abaxial surface — Yellow-Green Group 146B. Margins — With stipitate glands. Anthocyanin intonations — Greyed-Purple Group 183B present on the petiole of juvenile foliage. Prickles — None. Stipitate glands — Limited number of stipitate glands are present on the margins. Texture — Rugose on upper surface; smooth below. Strength — Strong.

*Rachis.*—Length — Average 10 mm. Diameter — Average 1.0 mm. Color — Yellow-Green Group 146A. Anthocyanin intonations — Greyed-Purple Group 183B present on the rachis of juvenile foliage. Margins — With very light pubescence. Prickles — None. Stipitate glands — None.

*Leaflets.*—Quantity — Normally 5 leaflets on normal leaves in middle of the stem. Dimensions — Average size of the terminal leaflet is 30 to 35 mm long and 20 mm wide. Shape — Obovate. Apex — Acute. Base — Obtuse. Margins — Serrulate; no undulation. Luster and texture, adaxial surface — Semi-glossy, rugose and glabrous. Luster and texture, abaxial surface — Matte, rugose, and glabrous. Juvenile foliage color, adaxial surface — Yellow-Green Group 147A. Juvenile foliage color, abaxial surface — Yellow-Green Group 147B. Mature foliage color, adaxial surface — Yellow-Green Group 147A. Mature foliage color, abaxial surface — Yellow-Green Group 147B. Anthocyanin intonations — Greyed-Red Group 182B present along the midrib of the adaxial surface, the margins, and the entire abaxial surface of juvenile leaflets. Venation — Reticulate. Petiolule — Dimensions — 0.5 mm long and 0.75 mm in diameter. Petiolule color, adaxial surface — Yellow-Green Group 146B. Petiolule color, abaxial surface — Yellow-Green Group 146C. Prickles — None present. Texture, adaxial surface — Smooth. Texture, abaxial surface — Smooth. Margins — Smooth with occasional stipitate glands.

Inflorescence:

*Inflorescence type.*—Panicles with 1 to 4 flower buds. Flowers are held upright.

*Blooming habit.*—Recurrent; floriferous.

*Size.*—60 mm tall and 50 mm wide, on average.

*Peduncle.*—Length — 50 to 60 mm average length. Diameter — 1.5 to 2.0 mm average diameter. Color — Yellow-Green Group 146B. Anthocyanin intonations — None present. Strength — Strong. Texture and pubescence — Smooth.

Flowering laterals: Present below the initiation of inflorescence. Generally one to two flowering lateral are present, with 1 flower per flowering shoot.

Bud:

*Bud form.*—Short; broad based.

*Size.*—Upon opening, 12 mm in length from base of receptacle to distal end of bud and 8 mm diameter at its widest point.

*Texture.*—Smooth.

*Color, as sepals first unfold.*—Red Group 46A.

*Color when one-quarter open, inner side.*—In between Red Group 46A and 46B.

*Color when one-quarter open, outer side.*—Red Group 46A.

Flower:

*Blooming habit.*—Recurrent; floriferous.

*Attitude of flower.*—Flowers are held upright.

*Pedicel.*—Surface — Nearly glabrous with a limited number of stipitate glands. Length — 30 to 40 mm. Diameter — 2.0 to 3.0 mm. Color — Yellow-Green Group 146B. Anthocyanin intonations — None. Strength — Somewhat strong. Texture — Glabrous with a limited number of stipitate glands.

*Calyx.*—General — Comprised of five polysepalous sepals, with moderately strong foliaceous appendages present on three of the five sepals. Diameter of calyx — 14 mm, at anthesis. Sepals — Color, adaxial surface — Yellow-Green Group 147C. Color, abaxial surface — Yellow-Green Group 146B. Anthocyanin intonations — None. Size — 15 mm long and 8 mm wide, on average. Apex — Cirrose to apiculate. Base — Flat at union with receptacle. Quantity — Five. Texture, adaxial surface — Pubescent. Texture, abaxial surface — Lightly pubescent. Margins — Entire; pubescent with occasional stipitate glands. Stipitate glands — Limited amount present.

*Corolla.*—Habit; type — Very double. General shape of corolla — Cupped rosette. Shape of corolla when viewed from the side — Upon opening, upper portion — Flat. Upon opening, lower portion — Flat. Open flower, upper portion — Flattened convex. Open flower, lower portion — Flattened convex. Dimensions — Medium for a miniature rose. When open, the average flower diameter is 50 mm and the average flower height is 15 mm. Fragrance — None. Duration — On the plant 15 to 20 days. Senesced petals drop away cleanly. Petals — Petal count — 50 petals under normal conditions. Petal reflex — Slightly reflexed. Timing of petal reflex — Simultaneously. Petal margin — Entire. Petal shape — Obovate. Apex — Obtuse. Base — Obtuse. Dimensions — 10 to 20 mm long and 15 to 20 mm wide. Texture, inner surface — Smooth. Texture, outer surface — Smooth. Petal color, upon opening — Outermost petals, inner surface — Marginal Zone — Red Group 46B. Middle Zone — Orange Group 24C. Basal Zone — A combination of Red Group 46B and Orange Group 24C. Outermost petals, outer surface — Marginal Zone — Red Group 46B. Middle Zone — Red Group 46B. Basal Zone — Red Group 46B. Innermost petals, inner surface — Marginal Zone — Red Group 46C. Middle Zone — Yellow-Orange Group 19B. Basal Zone — A combination of Red Group 44C. Innermost petals, outer surface — Marginal Zone — Red Group 53C. Middle Zone — Red Group 53C. Basal Zone — Red Group 53C. Basal petal spots, upon opening — No distinctive coloration at the petal base is observed. Petal color, after opening — Outermost petals, inner surface — Marginal Zone — Red Group 45A. Middle Zone — Greyed-Yellow Group 162D. Basal Zone — Greyed-Yellow Group 162D. Outermost petals, outer surface — Marginal Zone — Red Group 46B. Middle Zone — Red Group 46B. Basal Zone — Red Group 46B. Innermost petals, inner surface — Marginal Zone — Red Group 45A. Middle Zone — Greyed-Yellow Group 162D. Basal Zone — Greyed-Yellow Group 162D. Innermost petals, outer surface — Marginal Zone — Red Group 45A. Middle Zone — Red Group 45A. Basal Zone — Red Group 45A. Basal petal spots, after opening — No distinctive coloration at the petal base is observed. General Tonality — Red Group 46B. No change in general tonality at the end of the tenth day. Thereafter the general tonality is Red Group 47A. Petaloids — Quantity — 25 petaloids per flower, on average. Dimensions — Highly variable; approximately 7 to 10 mm long and 4 to 6 mm wide. Color, inner surfaces — Marginal Zone — Red Group 45B. Middle Zone — Red Group 45B. Basal Zone — Yellow-Orange Group 19C. Color, outer surfaces — Marginal Zone — Red Group 45B. Middle Zone — Red Group 45B. Basal Zone — Red Group 45B. Margins — Entire; undulated. Shape — Highly variable with some being obovate, some elliptical, others spatulate. Apex — Acute and obtuse. Base — Cuneate and attenuate. Texture, inner and outer surfaces — Smooth.

Reproductive organs:

*Stamens.*—Quantity — Approximately 10, irregularly arranged around the styles. Anthers — Shape — Reniform. Dimensions — 0.5 mm long and 0.5 mm wide, on average. Color — Yellow Group 9C. Pollen — Very scarce. Pollen Color — Yellow Group 3C. Filaments — Color — Yellow Group 9C. Length — 2 mm.

*Pistils.*—Quantity — Average; approximately 25. Stigmas — Dimensions — 0.75 mm long and 0.75 mm wide. Location — Superior in position to anthers. Color — Yellow Group 10C, and suffused with Greyed-Red Group 180D. Styles — Length — Approximately 6 mm long. Color — Yellow-Green Group 144C.

*Ovary.*—Dimensions — 4 mm long and 2 mm in diameter. Color — Green-White Group 157A.

*Receptacle.*—Shape — Funnel-shaped. Dimensions — Approximately 5 mm high and 7 mm wide. Surface — Glabrous and rugose. Color — Yellow-Green Group 146B.

Hips and seed formation: Not observed.

Comparisons with the parent: The new rose plant may be distinguished from its seed parent, an unnamed *Rosa hybrida* seedling, by the characteristics described in Table 1.

TABLE 1

| Characteristic | 'KORpot073' | Unnamed seed parent |
|---|---|---|
| Flower size. | Medium. | Small. |
| Flower color. | Red. | Apricot. |
| Flower type; petal count. | Very double. | Semi-double. |

The new rose plant may be distinguished from its pollen parent, *Rosa hybrida* 'RUId155a', by the characteristics described in Table 2.

TABLE 2

| Characteristic | 'KORpot073' | 'RUId155a' |
|---|---|---|
| Flower color. | Red. | Salmon orange. |
| General flower shape. | Cupped rosette. | Pointed. |
| Flower shelf life. | Very good. | Average. |

Comparison with the most similar *Rosa* cultivar known to the inventor: For a comparison, several physical characteristics of the *Rosa hybrida* variety 'KORpot040', a rose variety from the same inventor which is described and illustrated in U.S. Plant Pat. No. 27,221, are compared to 'KORpot073' in Table 3.

TABLE 3

| Characteristic | 'KORpot073' | 'KORpot040' |
|---|---|---|
| Bud form. | Short. | Long. |
| Petal count. | 50. | 75. |
| Terminal leaflet dimensions. | 30 to 35 mm long and 20 mm wide. | 40 to 55 mm long and 20 to 25 mm wide. |

That which is claimed:

1. A new and distinct variety of rose plant named 'KORpot073', as described and illustrated herein.

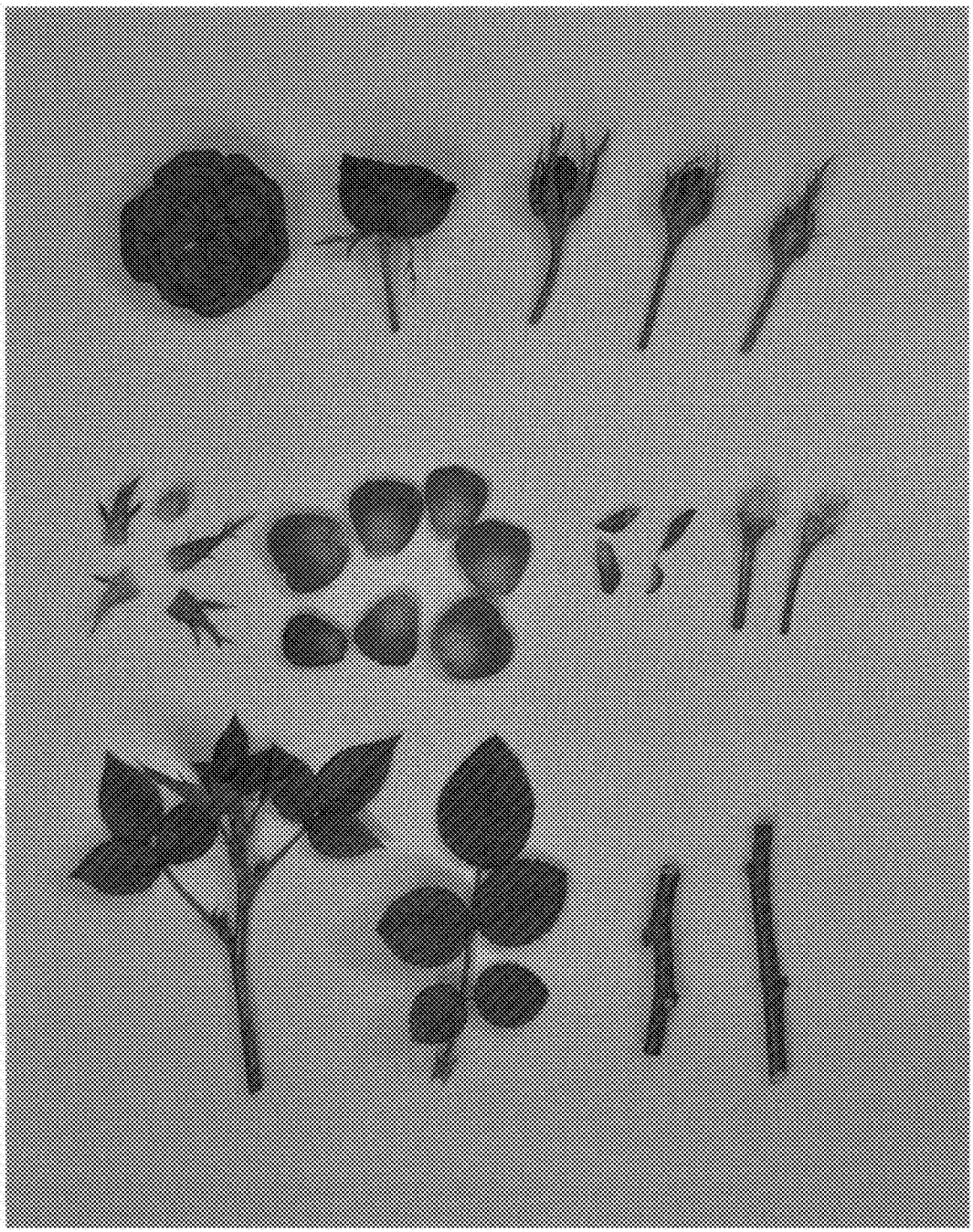

* * * * *